United States Patent
Cho et al.

(10) Patent No.: US 9,067,021 B2
(45) Date of Patent: Jun. 30, 2015

(54) NEEDLELESS INJECTOR

(76) Inventors: Min-Su Cho, Incheon (KR); Chang-Hee Lee, Busan (KR)

(*) Notice: Subject to any disclaimer, the term of this patent is extended or adjusted under 35 U.S.C. 154(b) by 293 days.

(21) Appl. No.: 13/637,638

(22) PCT Filed: Jan. 25, 2011

(86) PCT No.: PCT/KR2011/000497
§ 371 (c)(1),
(2), (4) Date: Apr. 11, 2013

(87) PCT Pub. No.: WO2011/149176
PCT Pub. Date: Dec. 1, 2011

(65) Prior Publication Data
US 2013/0190685 A1    Jul. 25, 2013

(30) Foreign Application Priority Data
May 28, 2010    (KR) .......................... 10-2010-0050505

(51) Int. Cl.
*A61M 5/30* (2006.01)
*A61M 5/178* (2006.01)
*A61M 5/315* (2006.01)
*A61M 5/24* (2006.01)
*A61M 5/31* (2006.01)
*A61M 5/20* (2006.01)

(52) U.S. Cl.
CPC .............. *A61M 5/30* (2013.01); *A61M 5/1782* (2013.01); *A61M 5/31533* (2013.01); *A61M 2005/2411* (2013.01); *A61M 2005/3114* (2013.01); *A61M 5/31548* (2013.01); *A61M 5/31543* (2013.01); *A61M 2005/2073* (2013.01); *A61M 2005/202* (2013.01)

(58) Field of Classification Search
CPC ..................... A61M 5/31533; A61M 5/31543; A61M 5/31548; A61M 5/31551; A61M 5/31555; A61M 2005/202; A61M 2005/2411; A61M 5/1782; A61M 2005/3114; B65B 3/00
USPC ......... 604/57–64, 68–72, 134–137, 152, 187, 604/208–211
See application file for complete search history.

(56) References Cited

U.S. PATENT DOCUMENTS

| | | | | |
|---|---|---|---|---|
| 4,165,800 A * | 8/1979 | Doherty et al. | .................. | 185/39 |
| 5,782,802 A * | 7/1998 | Landau | ........................... | 604/68 |
| 2006/0089594 A1 * | 4/2006 | Landau | ........................... | 604/68 |
| 2006/0270972 A1 * | 11/2006 | Lindmayer | ..................... | 604/68 |
| 2009/0048561 A1 * | 2/2009 | Burren et al. | .................. | 604/135 |

FOREIGN PATENT DOCUMENTS

| | | | |
|---|---|---|---|
| JP | 11123243 A | | 5/1999 |
| JP | 2003038643 A | | 2/2003 |
| KR | 1020090014169 A | | 2/2009 |

* cited by examiner

*Primary Examiner* — Theodore Stigell
*Assistant Examiner* — Lauren M Peng
(74) *Attorney, Agent, or Firm* — Schmeiser, Olsen & Watts LLP (57) ABSTRACT

The present invention relates to a needleless injector. The needleless injector includes a piston shaft with a plurality of holders on an outer surface in a circumferential direction; a cylinder assembly which slidably receives and supports the piston shaft in the forward and backward directions; and a plurality of balls which are received in the cylinder assembly and disposed around the piston shaft, the plurality of balls being movable in a radial direction and inserted into the plurality of holders when the piston shaft is moved in the backward direction. The injector also includes a trigger button slidably coupled to a rear end of the cylinder assembly to form a trigger end interrupting the movement of the balls inserted into the holders in the radial direction, the trigger button releasing the interruption of the trigger end when the piston shaft is slid in the forward direction.

14 Claims, 9 Drawing Sheets

NEEDLELESS INJECTOR

TECHNICAL FIELD

The present invention relates to a needleless injector and more particularly to a needleless injector improved to have a simple structure and to be used conveniently.

BACKGROUND ART

A needleless injector is an injector having no needle but provided to give an injection with high pressure.

Conventional needleless injectors include those shown in U.S. Pat. No. 5,704,911 "NEEDLESS HYPODERMIC JET INJECTOR"(registration date: Jan. 6, 1998), U.S. Pat. No. 5,891,086 "NEEDLE-LESS INJECTOR"(registration date: Apr. 6, 1999), U.S. Pat. No. 7,090,662 "DOSE DIAL AND DRIVE MECHANISMS SUITABLE FOR USE IN DRUG DELIVERY DEVICES"(registration date: Aug. 15, 2006) and etc.

However, such conventional needleless injectors have a complicated structure and thus are not easy to manufacture, generate noise during injection due to an impact. Also, they are comparably expensive.

DISCLOSURE

Technical Problem

Accordingly, it is an object of the present invention to provide a needleless injector having a simple structure, being easy to manufacture and convenient to use with low noise.

Technical Solution

In order to accomplish the above object, the present invention provides a needleless injector comprising: a piston shaft having at an outer surface a plurality of holder parts which are formed in a circular direction with a predetermined interval therebetween; a cylinder assembly penetrated therein through back and forth to accommodate and support the piston shaft so that the piston shaft is slidable back and forth; a plurality of balls accommodated in the cylinder assembly, disposed at a circumference of the piston shaft and provided to be movable at least in a radial direction, and being inserted into a plurality of the holder parts respectively if the piston shaft is retreated; a trigger button coupled to a rear end part of the cylinder assembly to be slidable back and forth, having a trigger end to block a plurality of the balls inserted in a plurality of the holder parts from moving in the radial direction, and releasing the blocking of the trigger end onto a plurality of the balls when sliding forward; first elastic pressing means pressing the piston shaft forward with respect to the cylinder assembly; and second elastic pressing means pressing the trigger button backward with respect to the cylinder assembly.

According to an aspect of the present invention, the cylinder assembly has a bush where the piston shaft is accommodated and supported, the bush has a plurality of guide holes in the circular direction with a predetermined interval therebetween to correspond to a plurality of the holder parts of the piston shaft, and the trigger end of the trigger button is disposed at an outer side of the bush to block movement of a plurality of the balls through a plurality of the guide holes.

According to an aspect of the present invention, the trigger button has adjacent to the trigger end a space part to accommodate a plurality of the balls moving in the radial direction when the balls are released from blocking of the trigger end.

According to an aspect of the present invention, the trigger end has a tip surface to block the radial movement of a plurality of the balls inserted in a plurality of the holder parts, and an inclined surface radially extending between the tip surface and the space part.

According to an aspect of the present invention, a plurality of the guide holes of the bush are formed inclined so that they are gradually enlarged in the radial direction.

According to an aspect of the present invention, the cylinder assembly comprises a main cylinder in which the piston shaft is inserted to be slidable, the main cylinder has at its front part a screw line receiving hole where an outer syringe member is coupled by screwing.

According to an aspect of the present invention, the cylinder assembly comprises a main cylinder in which the piston shaft is inserted to be slidable, a case cylinder in which the main cylinder is accommodated and supported, and a rear case coupled to a rear end part of the case cylinder to accommodate at least a part of the trigger button including the trigger end.

According to an aspect of the present invention, the main cylinder is formed with a screw line at its outer surface, the cylinder assembly further comprises a sleeve which is provided between the main cylinder and the case cylinder and formed at an inner surface with a screw line to be coupled to the main cylinder, the main cylinder is provided to adjust its length through screw coupling with the sleeve.

According to an aspect of the present invention, the main cylinder is provided with graduations at its outer surface to display an adjusted length on the basis of the sleeve.

According to an aspect of the present invention, the trigger button has a recess part at its side part which is inserted into a rear end part of the cylinder assembly to slide back and forth, and the cylinder assembly is provided with a release button which is perpendicularly coupled to the recess part to be operated to lock or unlock the trigger button.

According to an aspect of the present invention, the cylinder assembly has a loading recess part at its outer surface, and the needleless injector further comprises a shaft loading lever which includes a pressing cylinder part inserted into the front end part of the cylinder assembly to press a front end of the piston shaft, a lever part having an operating end part at a side part and a handle part at the other side part together with a hinge rotatably coupled to an end part of the pressing cylinder therebetween, a link part rotatably coupled to the operating end part at one end part, and a holder part rotatably coupled to the other end part of the link part and provided to be hung by the loading recess part.

According to an aspect of the present invention, the link part has at the one end part a plurality of coupling holes which are selectively coupled to the operating end part.

According to an aspect of the present invention, the needleless injector further comprises a connector for loading injection liquid into a nozzle which is inserted into a front end part of the cylinder assembly, and the connector comprises a nozzle mounting part where an end part of the nozzle is coupled and accommodated, and an ample mounting part having a protruding fin part which protrudes into an inner space and has a passage communicating with the nozzle mounting part, the nozzle mounting part and the ample mounting part are integrally formed.

According to an aspect of the present invention, the nozzle mounting part has a plurality of rotation coupling parts in a circular direction with a predetermined interval therebetween to be couple to or released from the end part of the nozzle when they are engaged with the end part of the nozzle and rotated relatively.

According to an aspect of the present invention, the nozzle mounting part is installed with a pressing rubber plate at a place where the end part of the nozzle is accommodated, the pressing rubber plate has at its center an injection hole which communicates with the nozzle.

Advantageous Effects

According to the needleless injector of the present invention as described above, the overall structure is simplified and it is easy to manufacture. Therefore, it is possible to supply with a comparably low price. As there is no movable parts in the locking state, impact noise can be minimized during injection. Anyone can easily use by loading a piston shaft with a loading lever.

BEST MODE

Figure 1:
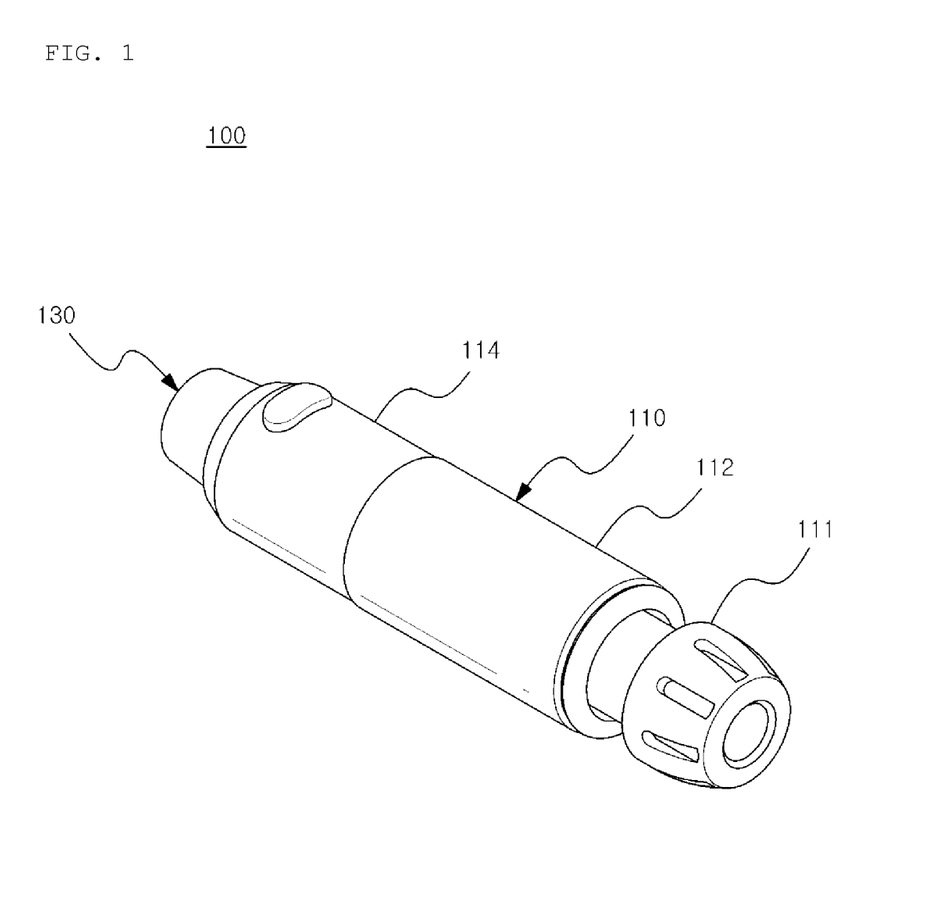
FIG. 1 is a perspective view of a needleless injector according to an exemplary embodiment of the present invention.

As shown in FIG. 1, a needleless injector 100 according to an exemplary embodiment of the present invention comprises a cylinder assembly 110, a trigger button 130 and etc.

The cylinder assembly 110 has a structure with a main cylinder 111 inserted into a case cylinder 112. A rear case 114 is combined to a rear end part of the case cylinder 112.

Figure 2:
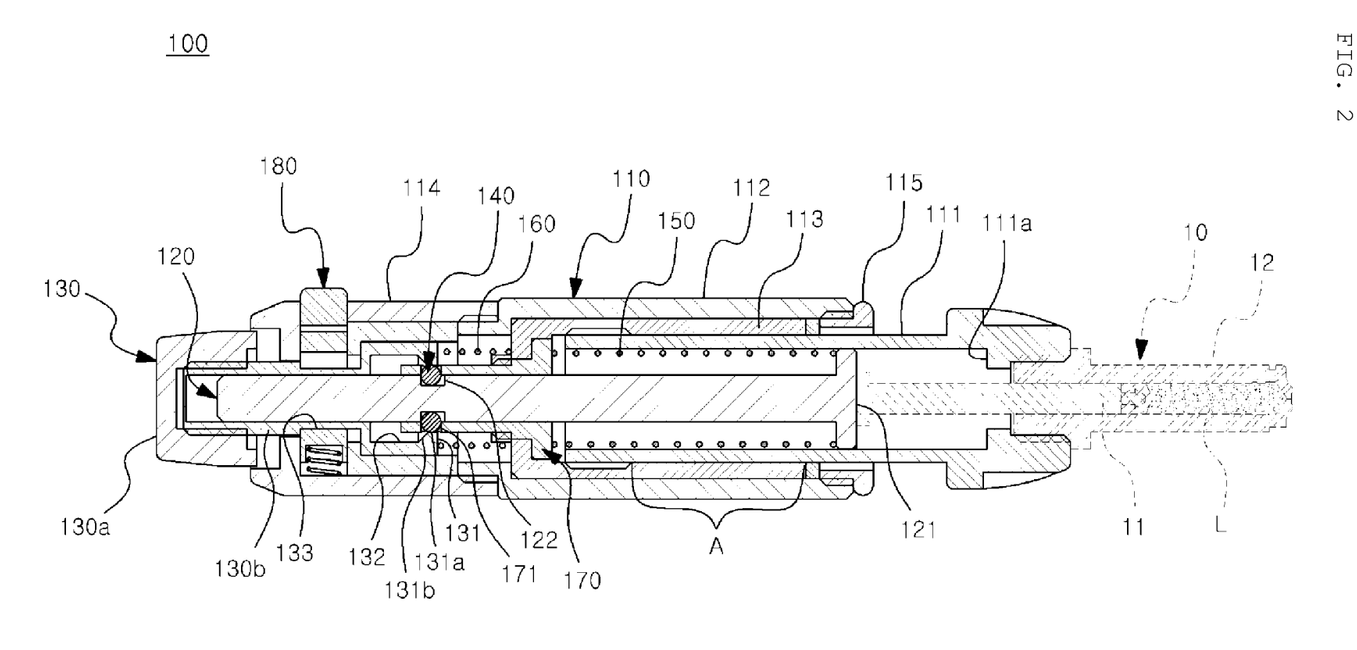
FIG. 2 is a sectional view of the needleless injector of FIG. 1 in a loaded state.

To describe the structure of the needleless injector 100 more specifically, the cylinder assembly 110 comprises, as shown in FIG. 2, a piston shaft 120 accommodated and supported in the cylinder assembly 110 to be slidable back and forth, the trigger button 130 combined to a rear end of the cylinder assembly 110 to be slidable, and a plurality of balls 140 disposed between a lateral surface of a rear part of the piston shaft 120 and a front end part of the trigger button 130 to have a locking, that is loading, function to the piston shaft 120.

The cylinder assembly 110 comprises the main cylinder 111 having a piston shaft 120 inserted therein to be slidable, a sleeve 113 having the main cylinder 111 therein to be coupled by screwing therebetween, the case cylinder 112 accommodating and supporting the sleeve 113 therein, and the rear case 114 coupled to the rear end part of the case cylinder 112.

A piston end 121 of the piston shaft 120 is inserted inside of the main cylinder 111 to be closely slidable. A screw line is formed at an outer surface of the cylinder to be coupled to an inner surface of the sleeve 113 by screwing together.

Correspondingly, a screw line is formed at the inner surface of the sleeve 113 to make a screw coupling area A with the main cylinder 111.

According to such a screw coupling area A, as shown in FIG. 2, the main cylinder 111 can be adjusted to move back (left) and forth (right) while the piston end 121 is at a fixed position, so that a cylinder volume in the main cylinder 111 can be adjusted.

This means a retreat length of a piston 11 of a syringe member 10 is adjustable and therefore an injection liquid L in a cylinder 12 of the syringe member 10 is adjustable.

In addition, the main cylinder 111 has graduations at its outer surface with a predetermined unit interval in an axial direction to display an adjusted length on the basis of the sleeve 113 which is relatively fixed, so that the injection dose is more precisely adjustable.

A plug 115 is coupled to a front opening of the case cylinder 112 to support a shaft loading lever (refer to FIG. 6) to be described later and to prevent damage on the case cylinder 112 and etc. due to the shaft loading lever.

The main cylinder 111 prevents a further forward movement of the front end of the piston shaft 120, that is piston end 121, with a stopper part 111a therein.

A spring 150 is inserted into an inner space of the main cylinder 111 and presses the piston end 121 of the piston shaft 120 with its front (right) end part.

A bush 170 penetrates into a rear end part of the main cylinder 111 to protrude into the rear case 114 at a rear side.

The bush 170 supports a back and forth slide movement of the piston shaft 120.

The bush 170 is inserted into a spring 160 at its outer surface. The spring 160 presses the trigger button 130 with its left end part in the rear (left) direction.

The piston shaft 120 is formed at its rear side outer surface with a plurality of holder parts 122 with a predetermined interval therebetween in a circular direction.

Correspondingly, a plurality of guide holes 171 are formed at a body part of the bush 170 with a predetermined interval therebetween in a circular direction.

As shown in the figure, each holder part 122 and each guide hole 171 is positioned to correspond to each other, and the ball 140 is inserted into the space formed by each holder 122 and each guide hole 171 together.

In this case, the ball 140 is prevented from moving in a radial direction by a trigger end 131 of the trigger button 130 which is disposed at the outer circumference.

As will be described later, the guide hole 171 of the bush 170 may be formed to be inclined in the radial direction to be gradually enlarged so that the ball 140 can move more easily in the radial direction.

For an amicable operation of the trigger button 130 in relation to the ball 140, the trigger end 131 has a tip surface 131a to support the ball 140 in the radial direction in a locking state as shown in FIG. 2, and an inclined surface 131b formed to gradually extend in the radial direction between the tip surface 131a and a space part 132 at the left side. The trigger button 130 is made of a button part 130a protruding in the rear direction of the rear case 114, and a trigger part 130b accommodated within the rear case 114 and integrally formed with the button part 130a.

The trigger part 130b includes the trigger end 131 to form the space part 132 to receive the ball which moves in the radial direction when unlocked.

Figure 3:
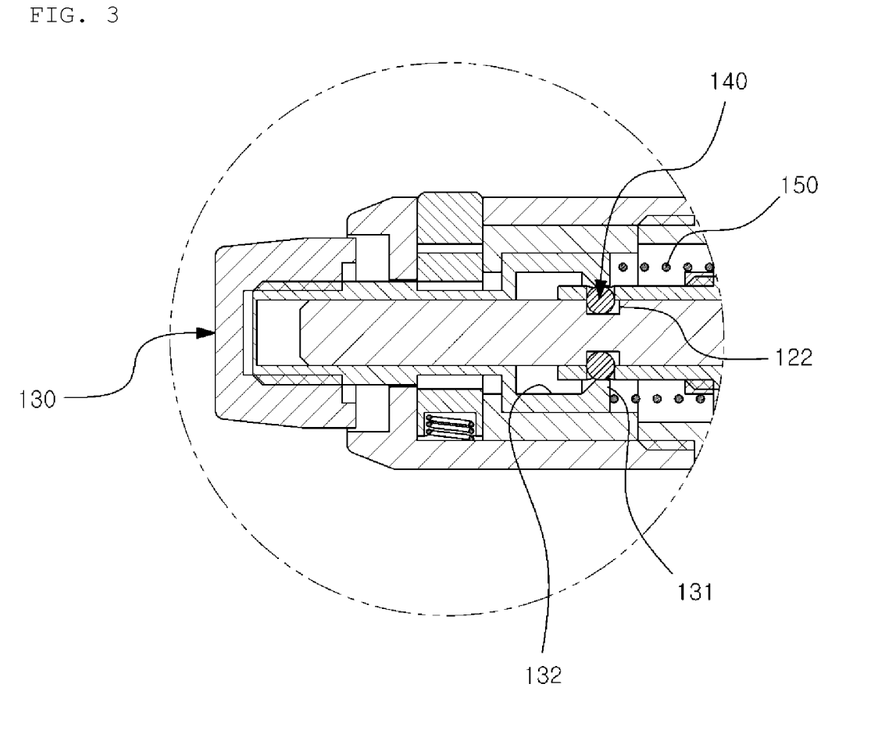
FIG. 3 and FIG. 4 are expanded sectional views showing an operational process of the needleless injector of FIG. 1.
Figure 4:
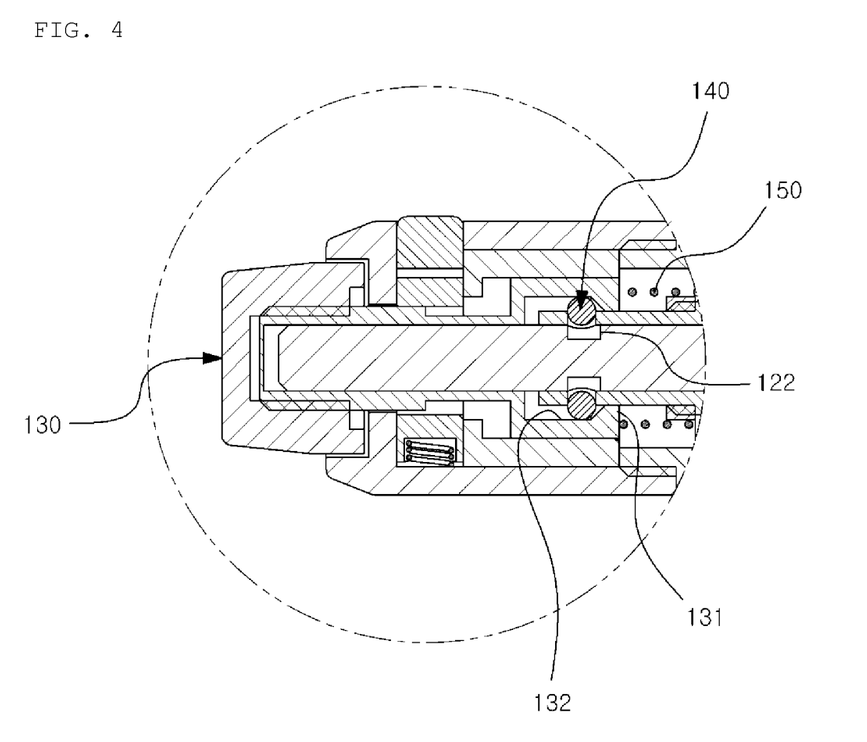

FIG. 3 and FIG. 4 show a process from the locking state of FIG. 2 to an unlocking state.

To release the locking state of the ball 140, the trigger button 130 is pushed in the right direction for the trigger end 131 to move forward, so that blocking the ball 140 in the radial direction is removed (refer to FIG. 4).

Then, the piston shaft 120 starts to be moved by the spring force (150, refer to FIG. 2) in the right direction. In this process, the ball 140 is pushed outward by a step of the holder part 122 of the piston shaft 120 to be received in the space part 132 which is located at the outer side.

Then, the piston shaft 120 moves in the right direction without troubles in a state of preventing inflow of the ball 140 with an outer surface of its rear part having a uniform radius, so that the unlocking due to the ball 140 ends.

Figure 5:
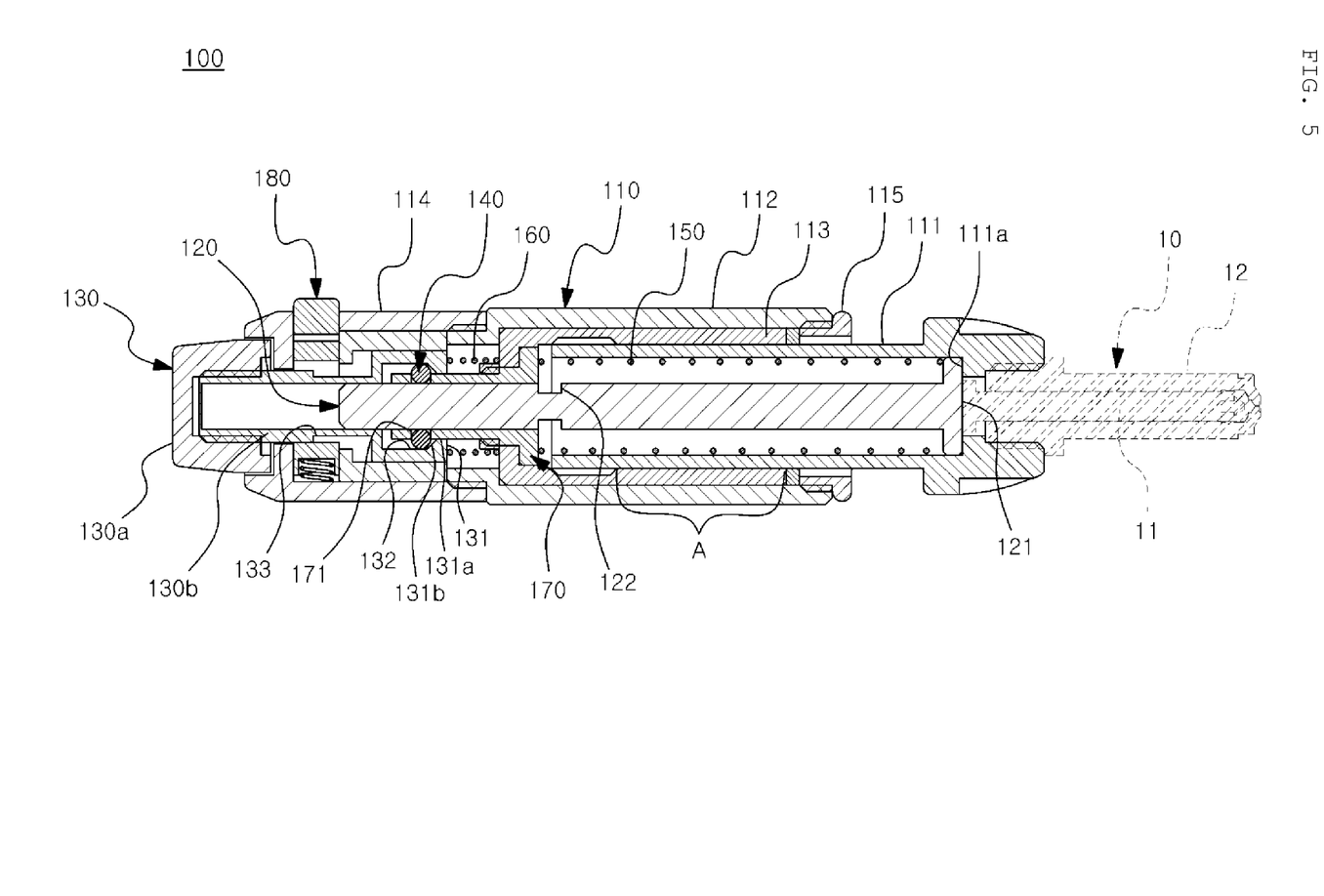
FIG. 5 is a sectional view of the needleless injector of FIG. 1 in a loading release state.

As the locking due to the ball 140 is released, the piston shaft 120 moves forward and the needleless injector 100 finally reaches the state of FIG. 5.

That is, the piston 11 of the syringe member 10 is pushed by the forward movement of the piston end 121, and the injection liquid L (refer to FIG. 2) in the cylinder 12 has been ejected.

The ball 140 still remains in the space part 132 to be supported by the outer surface of the piston shaft 120.

Referring to FIG. 2, the trigger button 130 has a recess part 133 at a side part of the cylindrical trigger part 130b which slides back and forth for the safety of the loaded needleless injector 100. Correspondingly, the rear case 114 is provided with a release button 180 which is perpendicularly coupled to and released from the recess part 133.

Therefore, the trigger button 130 can be operated only when the release button 180 is pushed, so that safely in use can be achieved.

Figure 6:
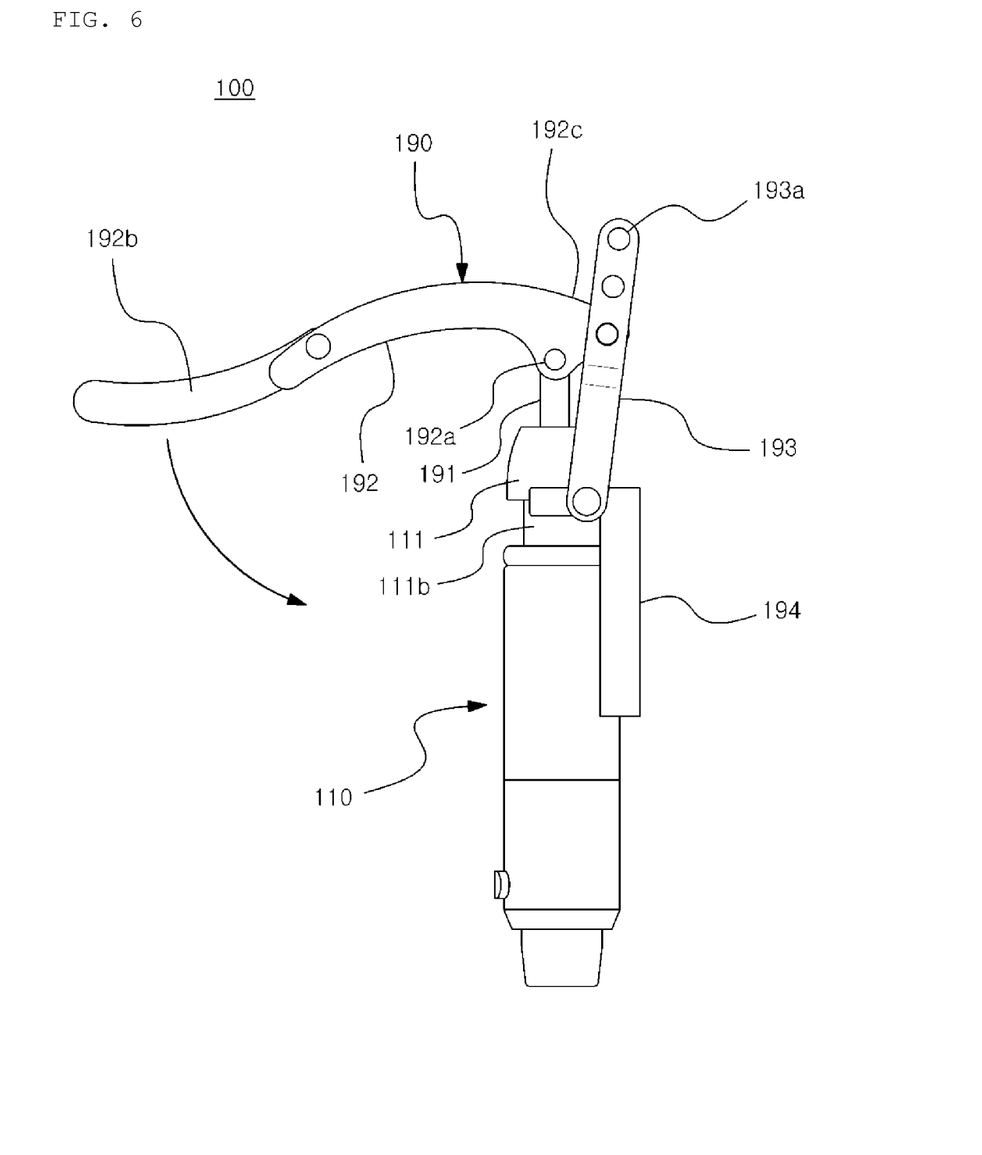
FIG. 6 is a schematic view for describing the loading process of the needleless injector of FIG. 1.

FIG. 6 shows a usage of a shaft loading lever 190 as an accessory of the needleless injector 100. The shaft loading lever 190 has a pressing cylinder part 191 which is inserted into the front end part of the cylinder assembly 110. An upper end part of the pressing cylinder part 191 is Rotatably coupled to a lever part 192 through a hinge shaft 192a (refer to FIG. 7).

Figure 7:
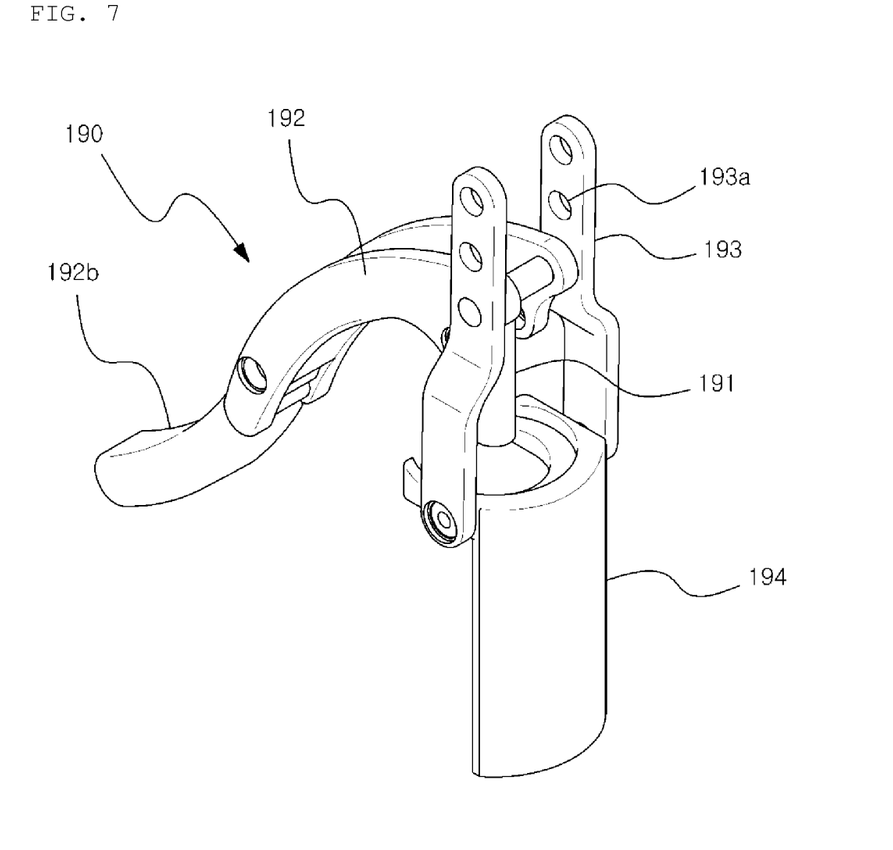
FIG. 7 is a perspective view of the shaft loading lever in FIG. 6.

The lever part 192 has a handle part 192b at the left side of the hinge shaft 192a, and has at the right side an actuating end part 192c through which the lever part 192 is rotatably coupled to a link part 193.

The link part 193 has at its upper end part a plurality of coupling holes 193a along a longitudinal direction to be selectively coupled to the actuating end part 192c.

A holder part 194 is rotatably coupled to a lower end part of the link part 193.

The holder part 194 is a part which is hung and fixed at the cylinder assembly 110. To this end, a loading recess part 111b is formed at the cylinder assembly 110.

The holder part 194 is inserted into the loading recess part 111b and hung at a protruding end of the main cylinder 111 to be supported.

In this state, if the handle part 192b of the lever part 192 is pushed downward, the pressing cylinder part 191 is moved downward within the main cylinder 111 to push the piston end (121, refer to FIG. 5) so that the piston shaft 120 retreats. Then, the holder part 122 receives the ball 140 (refer to FIG. 2) thus locking, that is loading, is accomplished.

Figure 8:
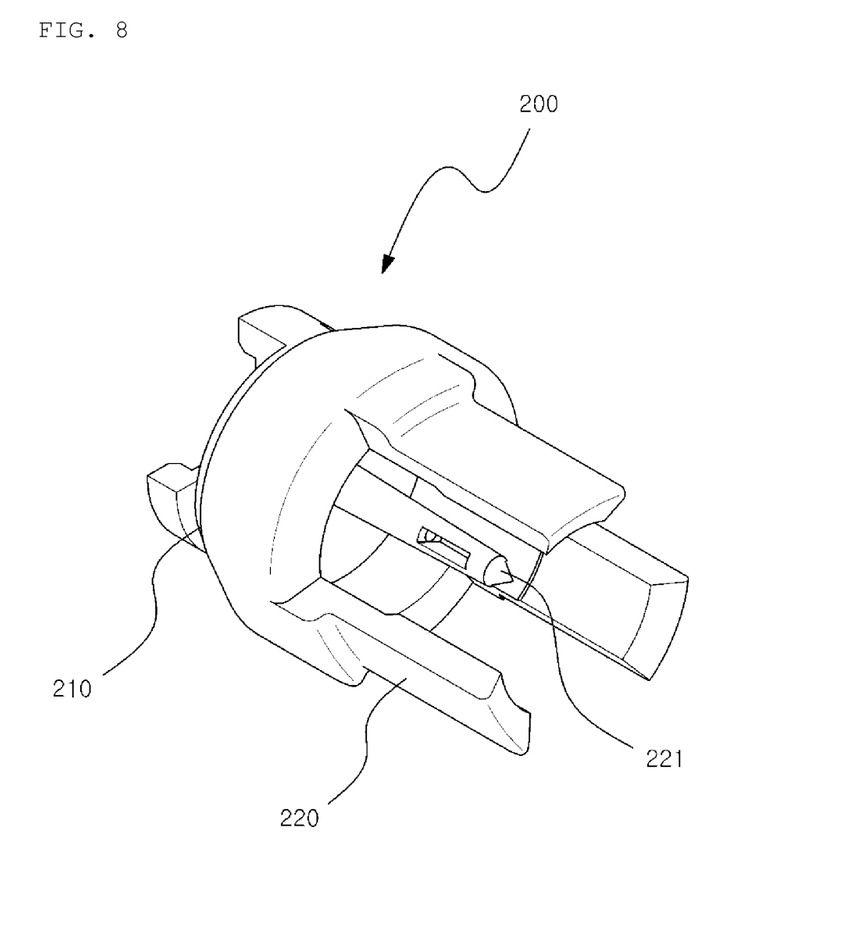
FIG. 8 is a perspective view of a connector which is an accessory of the needleless injector according to the exemplary embodiment of the present invention.

The needleless injector 100 described above comprises a connector 200 as described in FIG. 8 as its accessory for charging the injection liquid into the nozzle (10, refer to FIG. 2).

The connector 200 is formed at its both ends with a nozzle mounting part 210 where a front end part of the nozzle 10 is coupled and accommodated and an ample mounting part 220 where an ample filled with the injection liquid is coupled in the opposite direction therebetween.

Figure 9:
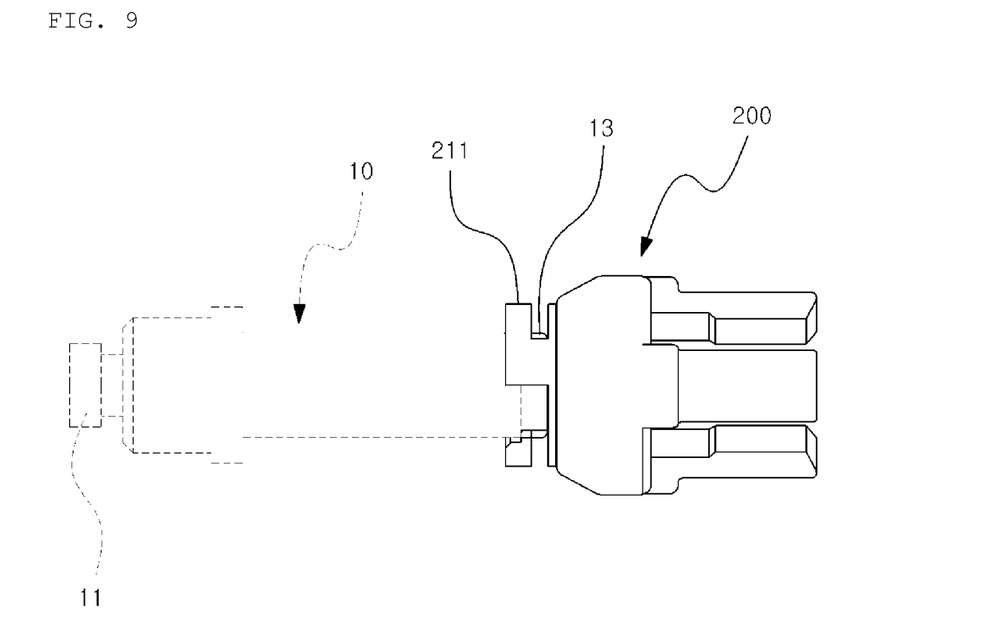
FIG. 9 and FIG. 10 are a side view and a side sectional view showing the connector of FIG. 8 in a combined state with a nozzle.

As shown in FIG. 9, the nozzle mounting part 210 is provided with a plurality of rotation coupling parts 211 with a predetermined interval therebetween in a circular direction.

The rotation coupling part 211 is engaged with the end part of the nozzle 10 and coupled thereto when rotated relatively.

Figure 10:
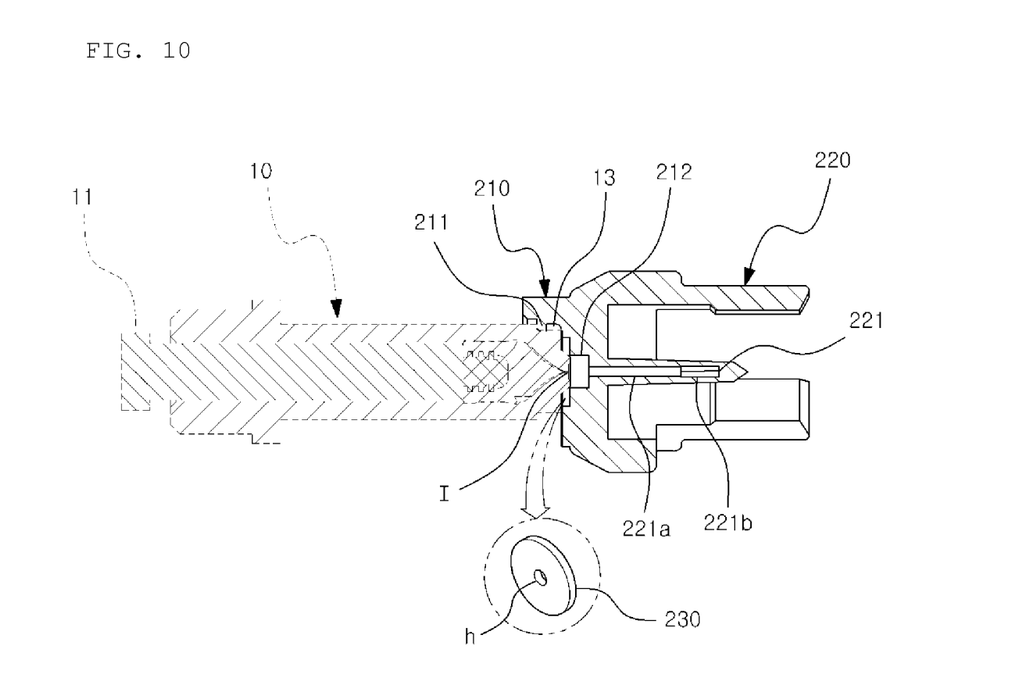

Accordingly, a protruding part 13 formed at the front end part of the nozzle 10 is inserted into the rotation coupling parts 211 to be coupled therein when the nozzle 10 and the nozzle mounting part 210 rotate relatively therebetween (refer to FIG. 10).

The end part of the nozzle 10 coupled to the nozzle mounting part 210, as shown in FIG. 10, has its nozzle inlet I to be accommodated in a space part 212.

In this case, a pressing rubber plate 230 is installed at an opening side of the space part 212 so that the nozzle inlet I can be completely sealed from the outside.

An injection hole h is formed at a center of the pressing rubber plate 230 to communicate with the nozzle inlet I.

The space part 212 communicates with an inner space of the ample mounting part 220 at its right side through a passage 221a and an injection opening 221b extending from a right end part of the passage 221a.

In the inner space of the ample mounting part 220 is provided a protruding fin part 221 which protrudes from the nozzle mounting part 210. The passage 221a and the injection opening 221b are formed within and at an end part of the protruding fin part 221 respectively.

According to the connector 200 as described above, the injection liquid discharged from an ample (not shown) which is mounted to the ample mounting part 220 moves to the space part 212 of the nozzle mounting part 210 at the left side through the injection opening 221b and the passage 221a and flows into the nozzle 10 through the nozzle inlet I.

Of course, such flow of the injection liquid is caused by generation of the negative pressure due to a retreat (in the left direction) of the piston 11 of the nozzle 10.

Although the needleless injector 100 according the exemplary embodiment of the present invention has been disclosed, various modifications, additions and substitutions are possible, without departing from the scope and spirit of the invention. Therefore, the above embodiment must be regarded as one example provided for description of the present invention, rather than to limit the present invention.

The invention claimed is:

1. A needleless injector comprising:
a piston shaft having at an outer surface a plurality of holder parts which are formed in a circular direction with a predetermined interval therebetween;
a cylinder assembly penetrated therein through back and forth to accommodate and support the piston shaft so that the piston shaft is slidable back and forth;
a plurality of balls accommodated in the cylinder assembly, disposed at a circumference of the piston shaft and provided to be movable at least in a radial direction, and being inserted into a plurality of the holder parts respectively if the piston shaft is retreated;
a trigger button coupled to a rear end part of the cylinder assembly to be slidable back and forth, having a trigger end to block a plurality of the balls inserted in a plurality of the holder parts from moving in the radial direction, and releasing the blocking of the trigger end onto a plurality of the balls when sliding forward;
first elastic pressing means pressing the piston shaft forward with respect to the cylinder assembly; and
second elastic pressing means pressing the trigger button backward with respect to the cylinder assembly, wherein the cylinder assembly has a loading recess part at its outer surface, and
the needleless injector further comprises a shaft loading lever which includes a pressing cylinder part inserted into the front end part of the cylinder assembly to press a front end of the piston shaft, a lever part having an operating end part at a side part and a handle part at another side part together with a hinge rotatably coupled to an end part of the pressing cylinder therebetween, a link part rotatably coupled to the operating end part at one end part, and a holder part rotatably coupled to another end part of the link part and provided to be hung by the loading recess part.

2. The needleless injector according to claim 1, wherein the cylinder assembly has a bush where the piston shaft is accommodated and supported, the bush has a plurality of guide holes in the circular direction with a predetermined interval therebetween to correspond to a plurality of the holder parts of the piston shaft, and the trigger end of the trigger button is disposed at an outer side of the bush to block movement of a plurality of the balls through a plurality of the guide holes.

3. The needleless injector according to claim 2, wherein the trigger button has adjacent to the trigger end a space part to accommodate a plurality of the balls moving in the radial direction when the balls are released from blocking of the trigger end.

4. The needleless injector according to claim 3, wherein the trigger end has a tip surface to block the radial movement of a plurality of the balls inserted in a plurality of the holder parts, and an inclined surface radially extending between the tip surface and the space part.

5. The needleless injector according to claim 2, wherein a plurality of the guide holes of the bush are formed inclined so that they are gradually enlarged in the radial direction.

6. The needleless injector according to claim 1, wherein the cylinder assembly comprises a main cylinder in which the piston shaft is inserted to be slidable, the main cylinder has at a front part a screw line receiving hole where an outer syringe member is coupled by screwing.

7. The needleless injector according to claim 1, wherein the cylinder assembly comprises a main cylinder in which the piston shaft is inserted to be slidable, a case cylinder in which the main cylinder is accommodated and supported, and a rear case coupled to a rear end part of the case cylinder to accommodate at least a part of the trigger button including the trigger end.

8. The needleless injector according to claim 7, wherein the main cylinder is formed with a screw line at its outer surface, the cylinder assembly further comprises a sleeve which is provided between the main cylinder and the case cylinder and formed at an inner surface with a screw line to be coupled to the main cylinder, the main cylinder is provided to adjust its length through screw coupling with the sleeve.

9. The needleless injector according to claim 8, wherein the main cylinder is provided with graduations at its outer surface to display an adjusted length on the basis of the sleeve.

10. The needleless injector according to claim 1, wherein the trigger button has a recess part at a side part which is inserted into a rear end part of the cylinder assembly to slide back and forth, and the cylinder assembly is provided with a release button which is perpendicularly coupled to the recess part to be operated to lock or unlock the trigger button.

11. The needleless injector according to claim 1, wherein the link part has at the one end part a plurality of coupling holes which are selectively coupled to the operating end part.

12. The needleless injector according to claim 1, wherein the needleless injector further comprises a connector for loading injection liquid into a nozzle which is inserted into a front end part of the cylinder assembly, and the connector comprises a nozzle mounting part where an end part of the nozzle is coupled and accommodated, and an ample mounting part having a protruding fin part which protrudes into an inner space and has a passage communicating with the nozzle mounting part, the nozzle mounting part and the ample mounting part are integrally formed.

13. The needleless injector according to claim 12, wherein the nozzle mounting part has a plurality of rotation coupling parts in a circular direction with a predetermined interval therebetween to be coupled to or released from the end part of the nozzle when they are engaged with the end part of the nozzle and rotated relatively.

14. The needleless injector according to claim 12, wherein the nozzle mounting part is installed with a pressing rubber plate at a place where the end part of the nozzle is accommodated, the pressing rubber plate has at its center an injection hole which communicates with the nozzle.

\* \* \* \* \*